Figure 1:
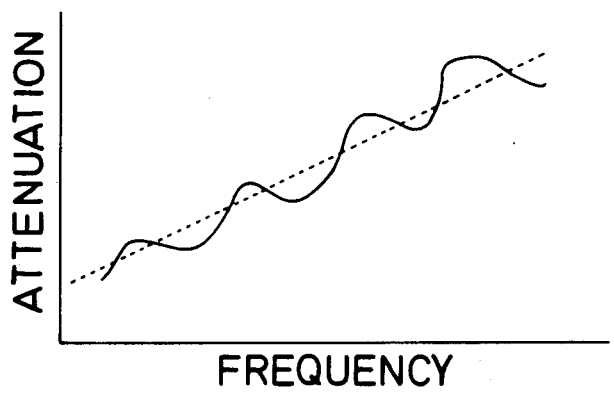

United States Patent [19]
Bell

[11] Patent Number: 4,788,853
[45] Date of Patent: Dec. 6, 1988

[54] MOISTURE METER

[75] Inventor: John F. M. Bell, Musselburgh, Scotland

[73] Assignee: Coal Industry (Patents) Limited, United Kingdom

[21] Appl. No.: 916,239

[22] Filed: Oct. 7, 1986

[30] Foreign Application Priority Data

Oct. 25, 1985 [GB] United Kingdom ............... 8526346

[51] Int. Cl.$^4$ .................... G01N 29/00; G01N 27/26
[52] U.S. Cl. .................... 73/73; 324/58.5 A
[58] Field of Search ......... 73/73; 324/58.5 A, 58.5 R, 324/58 A; 340/602; 364/556

[56] References Cited

U.S. PATENT DOCUMENTS

| | | | |
|---|---|---|---|
| 3,155,898 | 11/1964 | Chope | 324/58.5 A |
| 4,058,766 | 11/1977 | Vogel et al. | 324/61 R |
| 4,211,970 | 7/1980 | Fitzky et al. | 324/58.5 C |
| 4,246,784 | 1/1981 | Bowen | 374/117 |
| 4,283,953 | 8/1981 | Plona | 73/589 |
| 4,326,163 | 4/1982 | Brooke | 324/58.5 A |

FOREIGN PATENT DOCUMENTS

| | | | |
|---|---|---|---|
| 0000020 | 6/1978 | European Pat. Off. | 324/58.5 C |
| 1111384 | 4/1968 | United Kingdom. | |
| 1439375 | 6/1976 | United Kingdom. | |
| 2122741 | 1/1984 | United Kingdom. | |
| 2182149 | 5/1987 | United Kingdom | 324/58.5 A |

Primary Examiner—William A. Cuchlinski, Jr.
Assistant Examiner—W. Morris Worth
Attorney, Agent, or Firm—Stevens, Davis, Miller & Mosher

[57] ABSTRACT

A moisture meter and method for determining moisture content in a mass of material is provided. A source of microwave radiation selectively produces radiation having a plurality of different frequencies and directs the radiation into the mass of material. A support is provided for the material, which is substantially transparent to the radiation. A detector determines the emergent intensity of the radiation of each frequency traversing the mass of material and the support. A signal processing unit, responsive to (1) an intensity level of incident radiation directed into the mass of material, (2) a level of the emergent intensity of the radiation after passage through the mass of material and the support, and (3) the selective radiation frequencies, determines a value characteristic of moisture content based upon a slope of a plot of attenuation representing a difference between the intensity level of the incident radiation and the emergent radiation versus each of the plurality of different frequencies.

9 Claims, 2 Drawing Sheets

MOISTURE METER

This invention, concerns an improved moisture meter and more especially, it concerns a moisture meter for determining moisture in minerals, especially coal, using microwaves.

It is known to estimate moisture in, e.g., a bed of coal, by passing microwave energy through the bed and measuring the attenuation due to excitation of water molecules. We refer by way of background to our UK Patent No. 2,122,741B. This prior apparatus operates using a single fixed wavelength and does rely upon certain preconditions if it is to operate accurately; that is, the power output of the source must be constant, the geometry of the system must not vary and the density and depth of the coal bed must be constant. It is also possible for inaccuracies to be introduced if the composition of the coal varies, for example, if the coal is a blend whose constituents may vary in relative proportions. The known apparatus uses a Gunn effect oscillator as a source of microwaves in the 3 cm wavelengh band, and while this has been found to be stable under normal conditions of use, temperature variations can cause output variation and hence inaccuracy in the attenuation determination. Standing waves also significantly affect accuracy if there is any variation in the geometry of the system, e.g. caused by differing bed heights.

A novel moisture meter utilizing microwaves is now proposed which offers the possibility of overcoming most if not all the disadvantages of prior apparatus.

The present invention provides a moisture meter for a mass of material, comprising a source of microwave radiation capable of selectively producing a plurality of different frequencies, a support for the mass of material which support is substantially transparent to the microwave radiation, detector means capable of determining the intensity of microwave radiation of each selected frequency traversing the mass of material and the support, and signal processing means capable of determining a value characteristic of moisture content by derivation of the relationship between attenuation and frequency of said radiation.

Figure 2:
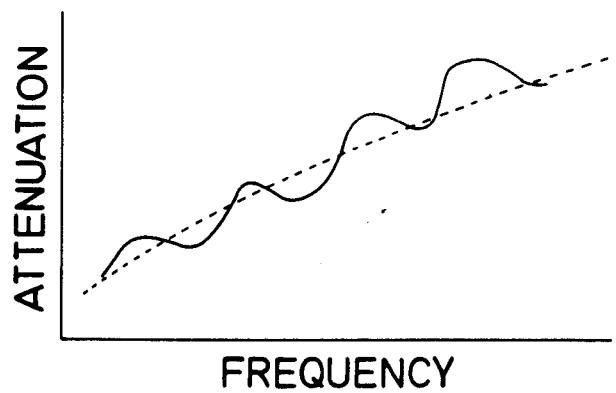

The invention also provides a method for determining moisture content in a mass of material, comprising selectively transmitting a plurality of frequencies of microwave radiation through the mass of material, determing the intensity of the radiation at each selected frequency after it has passed through the material and deriving a signal indicative thereof, processing the signals to determine attenuation and determining a value characteristic of moisture content by derivation from the relationship between attenuation and frequency. In one embodiment, the characteristic is the slope of the line of the plot of attenuation against frequency, particularly in the 4–8 GHz frequency band. In practice, the plot of attenuation against frequency for a given system is not a straight or curved line, but exhibits a cyclic variation dependent upon the geometry of the system, as reflections cause the path length to move in and out of phase. If the measured attenuation values are used as data for a curve fitting procedure, for example, using a regression program operated by a microprocessor, a first order line or second order curve can be found which is characteristic of a particular moisture content. Attached FIGS. 1 and 2 illustrate first order and second order curves and the cyclical variation in attenuation.

However, if the geometry of the system of source and mass of material should change, for example, by a change in the height of the bed of material, thus causing a change in the air gap between source and material, there will be a shift in the phase of the cyclical variation. Clearly, if the system is such that a shift can provide a fully out-of-phase plot in some circumstances, the opportunity for error in attenuation at any given frequency is quite large. Nonetheless, if a frequency scan is carried out according to the present invention for any given system geometry, the "best-fit" curve will be very similar to that resulting from a scan with a different system geometry since the average power will remain constant despite phase changes. It is therefore possible to calculate the "best-fit" curve for a set of results, and if previous calibration has shown the most suitable frequency for moisture determination, the intercept of the frequency with the curve will produce an attenuation characteristic of moisture content.

It is especially preferred that the characteristic is converted into a direct moisture content signal which may be displayed, recorded or transmitted. Conventional calibration may be used to enable the method of the invention to improve accuracy of moisture determination over prior methods. Further, the method can cope with lumps of coal of up to 5 cm in diameter.

The source of microwave radiation is preferably capable of emitting a scan of the different frequencies, and the breadth of the scan is preferably such as to permit an averaging out of, or other compensation for, the cyclical variations in attenuation caused by the standing waves generated in the system at the different frequencies utilized. Preferably, the scan is at least 0.5 octave, and may suitably be up to 5 octaves, although it may conveniently be about 1 octave. The frequency band chosen is conveniently within the range of 0.1 to 20 GHz, preferably in the range 2.0 to 12 GHz especially around 4–8 GHz, but this may be chosen according to the material and its expected moisture content; its thickness on the support etc. A practical controller of microwave signals is a Marconi Scalar Analyser 6500 which is capable of controlling an associated oscillator to generate 422 frequencies over 1 octave of microwave signals between 4 and 8 GHz. This device has not been proposed for use in moisture meters but is marketed as an aid to development of electronic components. The number of frequencies required for the scan is not critical provided that sufficient data is generated; it is preferred to run over at least 50, preferably at least 100 frequencies. The other necessary components are well known, including horn antenna and waveguide and do not form part of the present invention.

It is preferred to include means for detecting the level of radiation emitted from the source, preferably detected at or close to the surface of the material, to permit the signal processing means to determine a true attenuation i.e., eliminating attenuation occurring between the source and the surface of the material; this may be done by high speed sampling of the incident radiation level detected at the material surface and the emergent radiation level detected after passage through the material and support therefor, and comparison of these sampled levels.

The support for the sample may be a rotatable table as illustrated in UK Patent No. 2,122,741B or a static sample cell, but the present invention may be applied also to a conveyor belt, thus offering the possibility of on-line moisture monitoring. The material of the support may be selected from synthetic plastics material, of which polypropylene and polyvinyl chloride may be particularly mentioned, and conveyor belts for minerals, which may have a PVC layer laminated with a wear resistant layer, e.g. of a chlorinated polyethylene or "Neoprene" (Registered Trade Mark) may be found to be quite suitable.

The material being subjected to microwave radiation is suitably coal, but any other material which does not exhibit significant attenuation of microwave radiation in the relevant waveband may also be considered. These materials may include other minerals, unprocessed or processed vegetable matter, for example grain, products of or feedstocks for the chemical industry and the like.

The detector means will usually comprise a horn antenna, a semi-conductor diode and temperature compensating circuits which are conventional, and suitable detectors are commercially available. The detector means provides a signal indicative of the microwave radiation transmitted through the material and the support, attenuated by the moisture present (as well as by the material itself and possibly some slight attenuation caused by the support).

The signal processing means may suitably comprise a microprocessor, of which there are a number which may be utilized, connected and programmed by a competent electronics engineer. The signal processing means is required to derive a value for attenuation, either by comparing (1) the nominal or incident microwave energy with the attenuated or emerging transmitted energy or (2) a measured energy emission directly from the source with the transmitted energy or emergent energy level after passing through the material and support. We have found that, providing sufficient measurements are made at different frequencies, the plot of attenuation against frequency is a straight line or second order curve in the 4–8 GHz band, and the slope of the line is characteristic of moisture content. It is preferred to use the microprocessor to calculate a first order linear equation, using a regression program, which is of the type $$attenuation = gradient \times frequency + constant,$$

where the gradient is the slope of the plot resulting from the regression operation.

The gradient increases with moisture content, and the inherent attenuation of the material as well as its moisture content affect the "constant", which may be regarded as the intercept of the line on the attenuation axis.

A second order curve according to the equation:

$$Attenuation = constant_1 + constant_2 \times frequency + constant_3 \times frequency^2$$

is closer to the theoretical relationship between attenuation and frequency.

It is preferred also to provide to the microprocessor data on the density and thickness of the material. We have discovered that there is a direct and linear correlation between attenuation and both the density and bed depth of, e.g., a coal sample, i.e. the mass of the sample. It is therefore possible for the micro-processor to access this data and incorporate correction factors without the previously recommended attempts to obtain a constant bed depth and packing density, which tended to be expensive and complex in equipment and/or operator time. Such data may be obtained by methods known per se, including mechanical height measurement, e.g. using a trailing arm, ultrasonic ranging or optical (including infra-red) rangefinding techniques, and sample weights may be found e.g., by conventional belt weighers.

Figure 3:
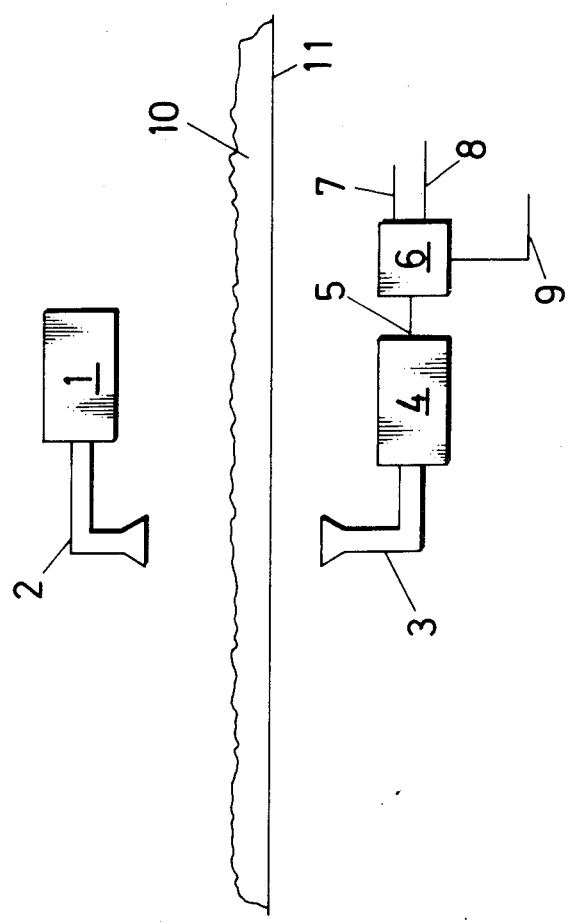

The invention will now be described by way of example only, with reference to the accompanying drawing, in which FIG. 3 is a schematic diagram of an apparatus according to the invention.

Referring to FIG. 3, a microwave source, 1, which is capable of producing radiation in frequencies within the 4–8 GHz band, has a waveguide and horn feed, 2. A corresponding horn and waveguide, 3 delivers the transmitted radiation to a semi-conductor-type detector, 4, which produces an output indicating a signal strength through line 5 to a processor unit, 6. The processor unit 6 also receives data on the frequency being emitted and the actual signal strength being emitted through line 7, and data on material density and bed height through line 8. The processor calculates the attenuation at each frequency, and by a regression program calculates the slope of the line of attenuation verses frequency for each sweep of frequencies across the band. The processor then compares the slope with calibration data and derives a signal directly corresponding to moisture content, which is transmitted through line, 9 to a control unit (not shown) where it is displayed. The material being sensed by the moisture meter is represented by a bed of material, 10, supported upon PVC conveyor belt, 11.

I claim:

1. A moisture meter for a mass of material, comprising:
    a source of microwave radiation for selectively producing radiation at a plurality of different frequencies and for directing said radiation into said mass of material,
    a support for the mass of material, which is substantially transparent to said radiation,
    detector means for determining an intensity of emergent radiation at each frequency traversing the mass of material and the support, and
    signal processing means, responsive to (i) intensity of incident radiation directed into said mass of material (ii) said intensity of said emergent radiation and (iii) said selectively produced radiation frequencies, for determining a value characterisitc of moisture content based upon a slope of a plot of attenuation representing a difference between intensity levels of said incident radiation and said emergent radiation at each of said plurality of different frequencies.

2. A moisture meter as claimed in claim 1, wherein said source emits frequencies within a range of 2.0 to 12 GHz.

3. A moisture meter as claimed in claim 2, wherein said source emits frequencies within a range 4 to 8 GHz.

4. A moisture meter as claimed in claim 1, wherein said source produces at least 100 frequencies.

5. A method for determining moisture content in a mass of material, comprising:
    selectively transmitting a plurality of frequencies of microwave radiation through the mass of material,
    determining the intensity of the radiation at each frequency before it has passed through the material and after it has passed through the material and providing signals indicative thereof, processing said signals to determine attenuation of intensity of said radiation during passage through the material at each frequency, and determining a value characterisitc of moisture content based upon a slope of a plot of said attenuation versus each of said frequencies.

6. A method as claimed in claim 5, wherein at least 100 frequencies are used in a scan across a frequency range.

7. A method as claimed in claim 5, wherein said frequencies are within a range 2.0 to 12 GHz.

8. A method as claimed in claim 7, wherein said frequencies are in a range 4 to 8 GHz.

9. A method as claimed in claim 5, wherein the material is coal.

* * * * *